Nov. 28, 1961 C. G. DUEHRSEN Plant Pat. 2,106
ROSE PLANT
Filed Dec. 27, 1960
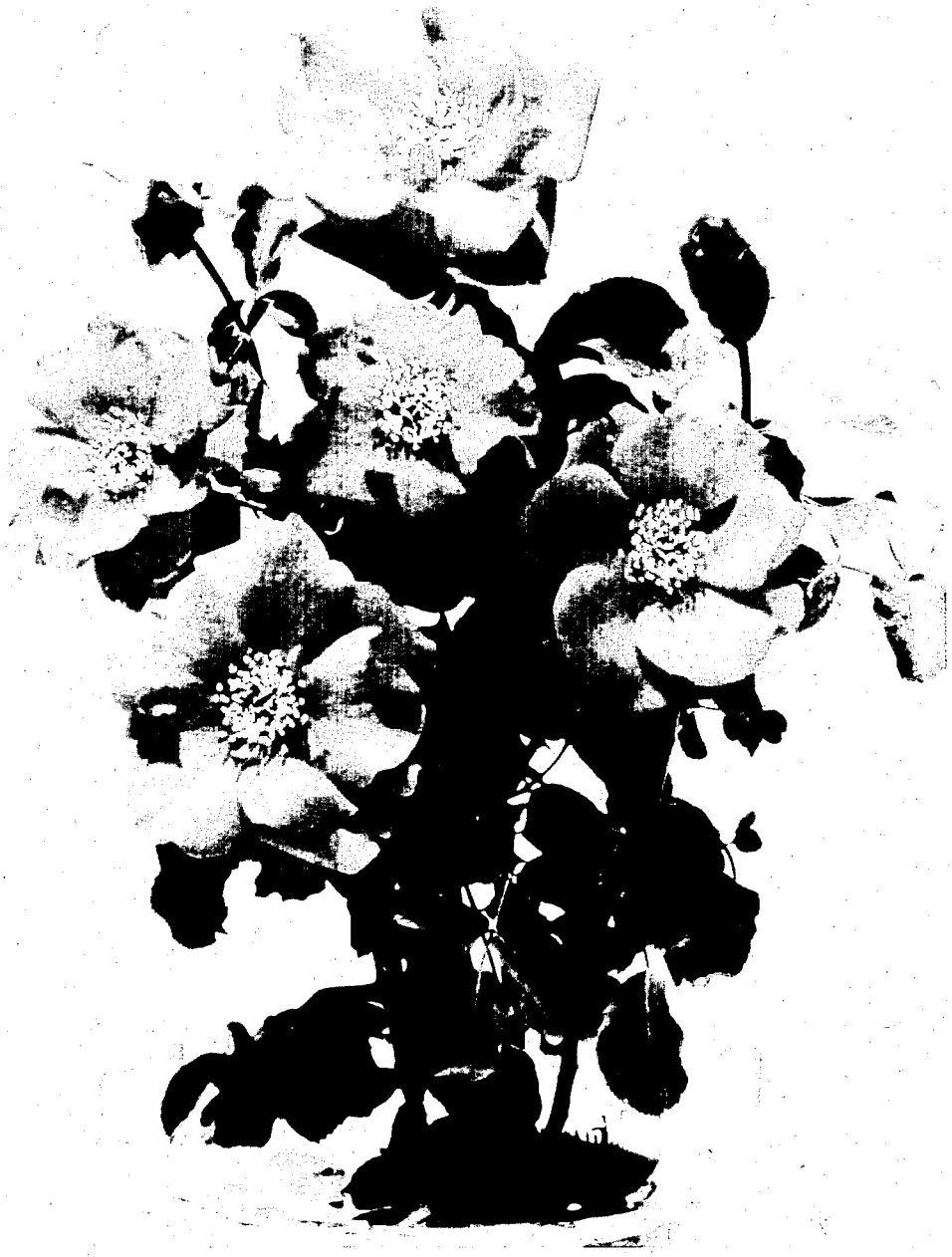
INVENTOR
Carl G. Duehrsen
BY Robb & Robb
ATTORNEYS United States Patent Office Plant Pat. 2,106
Patented Nov. 28, 1961

2,106
ROSE PLANT

Carl G. Duehrsen, Montebello, Calif., assignor to Constance A. Elmer, San Gabriel, Calif.

Filed Dec. 27, 1960, Ser. No. 78,796
1 Claim. (Cl. 47—61)

The present invention relates to a new and distinct variety of rose plant of the hybrid tea class, which was orginated by me by crossing an unnamed and unpatented seedling of "Charlotte Armstrong" (Plant Patent No. 455)×"Butterfly" (unpatented) with another unnamed and unpatented seedling of "Gruss an Teplitz" (unpatented) ×"Floradora" (unpatented).

As the result of this breeding, I have produced a new rose variety which is endowed with the following unique combination of desirable characteristics, which distinguish the same from its parents, as well as from all other varieties of which I am aware:

(1) A strong and vigorous habit of growth;

(2) Very dark green, glossy and leathery foliage which has good resistance to both mildew and black spot;

(3) A continuous blooming habit extending from very early spring until late fall;

(4) Long and strong flower stems;

(5) Very long, graceful and pointed buds;

(6) A large and attractive open flower size;

(7) A distinctive Brilliant Oriental Red general color tonality of the flowers in which the petals are edged with fiery red markings; and (8) Good keeping qualities of the flowers as cut flowers.

Asexual reproduction of my new variety by budding, as performed by me at Montebello, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Colour Chart of the British Colour Council, except where general color terms of ordinary dictionary significance are obvious:

Type: Hardy; tall; bush; outdoor; seedling; for cut flowers and for garden decoration.

Class: Hybrid tea.

Breeding: Seedling.

*Seed parent.*—An unnamed seedling of "Charlotte Armstrong"×"Butterfly."

*Pollen parent.*—An unnamed seedling of "Gruss an Teplitz"×"Floradora."

Propagation: Holds its distinguishing characteristics through succeeding propagations by budding.

*Flower*

Locality where grown and observed: Chino, California.

Continuity: Continuous.

Fragrance: Slight. Nature—tea.

Flowers borne: Several to stem; in irregular clusters; on strong, long stems ranging from 18 inches to 24 inches long.

Quantity of bloom: Free, outdoors.

Bud:

*Peduncle.*—Medium length; erect. Color—green.

*Before calyx breaks.*—Size—medium. Form—globular; with a conspicuous neck; with foliaceous appendages on the surface of the bud; with stout, entire foliaceous parts extending beyond the tip of the bud equal to ¼ or more of its length. Color—Oriental Red, Plate 8/19.

*As calyx breaks.*—Color—Cherry Red, Plate 7/22.

*As first petal opens.*—Size—medium. Form—globular. Color: outside—Oriental Red, Plate 8/19; inside—Cherry Red, Plate 7/22.

*Opening.*—Opens up well.

Bloom:

*Size (when fully open).*—Medium; from 3 inches to 4 inches in diameter.

*Petalage.*—Semi-double (two rows of petals); stamens not hidden; arranged regularly.

*Form.* — Globular at first, but becoming open-cupped; petals at first being very loosely reflexed and remaining so at maturity.

Petals:

*Texture.*—Thick; leathery; velvety.

*Shape.*—Outside—obovate; with irregular margin. Inside—obovate; with irregular margin.

This description of a newly opened flower was made from a rose grown outdoors in the month of September at Montebello, California:

*Color.*—Outer petal: outside surface—Cherry Red, Plate 7/22; inside surface — Oriental Red, Plate 8/19. Inner petal: outside surface—Cherry Red, Plate 7/22; inside surface—Oriental Red, Plate 8/19.

This description was made from a rose that was cut from outdoors and that was open for three days in the month of September at Montebello, California:

*Color.*—Outer petal: outside surface—Cherry Red, Plate 7/22; inside surface — Oriental Red, Plate 8/19. Inner petal: outside surface—Cherry Red, Plate 7/22; inside surface—Oriental Red, Plate 8/19.

*General color effect.*—Newly opened flower—Brilliant Oriental Red. 3-days open—Brilliant Oriental Red.

*Behavior.*—Drop off cleanly.

*Flower longevity.*—On bush in garden—4 days during months of April through October. Cut roses grown outdoors and kept at living room temperatures—4 days in July.

*Reproductive organs*

Stamens: Many; irregularly arranged about pistils.

Filaments: Short; with anthers. Color—reddish.

Anthers: Large; all open at once. Color—yellow.

Pollen: Abundant. Color—lemon.

Pistils: Medium number.

Styles: Even; short; medium caliper; bunched.

Stigma: Color—brown.

Ovaries: All enclosed in calyx.

Hips: Globular; smooth; walls fleshy.

Sepals: Permanent; long; straight; spear-shaped. Color—light green.

Seeds: Few; medium size.

*Plant*

Foliage:

*Leaves.*—Compound of 5 leaflets; normal abundance; leathery; glossy.

*Leaflets.*—Shape—round, with apex from obtuse to mucronate. Base—round. Margin—serrate.

*Color.*—Mature: upper surface—Parsley Green, Plate 00962; under surface—Spinach Green, Plate 0960. Young: upper surface—Maroon, Plate 1030; under surface—Oxblood Red, Plate 00823.

*Rachis (the supporting stem of the compound leaf).*—Medium caliper. Upper side—grooved. under side—smooth.

*Stipules.*—Medium length; with short points turning out at an angle of less than 45°.

*Disease resistance.*—Good resistance to mildew and black spot, as determined from comparison with other varieties grown under comparable cultural conditions at Chino, San Gabriel and Montebello, California.

Growth:

*Habit.*—Upright.

*Growth.*—Vigorous.

*Canes.*—Medium caliper.

*Main stems.*—Color—green. Thorns—few; hooked downward; with narrow base. Prickles—none. Hairs—none.

*Branches.* — Color — green. Thorns — few; short; hooked downward; with narrow base. Prickles—none. Hairs—none.

*New shoots.*—Color—green. Thorns—few; short; with narrow base. Prickles—none. Hairs—none.

I claim:

A new and distinct variety of rose plant of the hybrid tea class, substantially as herein shown and described, characterized particularly as to novelty by the unique combination of a strong and vigorous habit of growth, very dark green, glossy and leathery foliage which has good resistance to both mildew and black spot, a continuous blooming habit extending from very early spring until late fall, long and strong flower stems, very long, graceful pointed buds, large open flower size, a distinctive Brilliant Oriental Red general color tonality of the flowers, with the flower petals being edged with fiery red markings, and good keeping qualities of the flowers as cut flowers.

No references cited.